US00PP10276P

United States Patent [19]

Guillier

[11] Patent Number: Plant 10,276

[45] Date of Patent: Mar. 10, 1998

[54] APPLE TREE NAMED 'DELBLUSH'

[75] Inventor: Gérard Guillier, Commentry, France

[73] Assignee: Société des Pépiniéres et Roseraies Georges Delbard, Commentry, France

[21] Appl. No.: 654,169

[22] Filed: May 28, 1996

[51] Int. Cl.[6] ..... A01H 5/00

[52] U.S. Cl. ..... Plt./35.1

[58] Field of Search ..... Plt./35.1, 34.1, Plt./35

[56] References Cited

U.S. PATENT DOCUMENTS

| | | | |
|---|---|---|---|
| P.P. 4,731 | 6/1981 | Stark, Jr. | Plt./35.1 |
| P.P. 6,225 | 7/1988 | Tobutt | Plt./35.1 |
| P.P. 6,294 | 9/1988 | Merrill | Plt./35.1 |
| P.P. 7,209 | 4/1990 | Wick | Plt./35.1 |
| P.P. 7,851 | 4/1992 | Simmons | Plt./35.1 |

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

The new cultivar was formed through the crossing of the 'Golden Delicious' and 'Grifer' apple cultivars. Attractive yellow fruit commonly having an orange blush or overcolor extending over a potion of the skin is formed that is ready for harvest mid to late in the season. The extent of the overcolor on the mature fruit is influenced by the position of the fruit on the tree and the level of sunlight that is encountered during ripening. The fruit is excellent in flavor and texture. The fruit flesh well resists darkening upon exposure to ambient conditions. Additionally, attractive medium green foliage having an acuminate apex and a rounded base is formed.

3 Drawing Sheets

SUMMARY OF THE INVENTION

The new cultivar of apple plant of the present invention was created by artificial pollination wherein two parents were crossed in the hope they would contribute the desired characteristics. The female parent (i.e., the seed parent) was the 'Golden Delicious' cultivar (non-patented in the United States). The male parent (i.e., the pollen parent) was the 'Grifer' cultivar (non-patented in the United States). The parentage of the new cultivar can be summarized as follows:

'Golden Delicious'×'Grifer'.

The seeds resulting from the above pollination were sown and 275 small plantlets were obtained which were physically and biologically different from each other. Selective study resulted in the identification of a single plant of the new variety.

It was found that the new cultivar of the present invention exhibits the following combination of characteristics:

(a) forms attractive yellow fruit of excellent flavor and texture when mature commonly possessing an orange overcolor on a portion of the skin,
(b) forms fruit flesh that well resists darkening upon exposure to ambient conditions,
(c) forms attractive medium green foliage having an acuminate apex and a rounded base, and
(d) commonly yields an apple crop mid to late in the season.

The new apple cultivar has been found to undergo asexual propagation and can be readily reproduced by conventional routes, such as budding (i.e, eye grafting). This asexual reproduction as performed in France has demonstrated that the characteristics of the new cultivar are strictly transmissible from one generation to another and are firmly fixed. Representative rootstocks that can be utilized with the new cultivar include the PAJAM® brand of 1 Lancep and 2 Cepiland, M26, M9EMLA and M9NAKB. The particularly preferred rootstock is the PAJAM® brand of 2 Cepiland.

Other rootstocks similarly can be selected taking into consideration the soil conditions and other environmental conditions that are encountered at a specific growing site.

The new cultivar of the present invention has been named 'Delblush'.

BRIEF DESCRIPTION OF THE PHOTOGRAPHS

The accompanying photographs show typical specimens of the new cultivar as depicted in color as nearly true as it is reasonably possible to make the same in color illustrations of this character. The plant material shown in the photographs was budded on PAJAM® brand of 2 Cepiland rootstock and was grown at Malicorne, Commentry, France. A measuring stick in centimeters is included in FIGS. 1, 3 and 4 so that typical size information readily can be ascertained.

FIG. 1 illustrates typical fruit specimens of the new variety. At the top row apples are illustrated which exhibit various stages of maturity. The depicted fruit coloration also is influenced by the position of the fruit on the tree and the level of sunlight that is encountered during ripening. At the bottom row from left to right are depicted a bottom view of a typical mature fruit, a cross-sectional view of a typical mature fruit, and a top view of a typical mature fruit.

DETAILED DESCRIPTION

Figure 1:
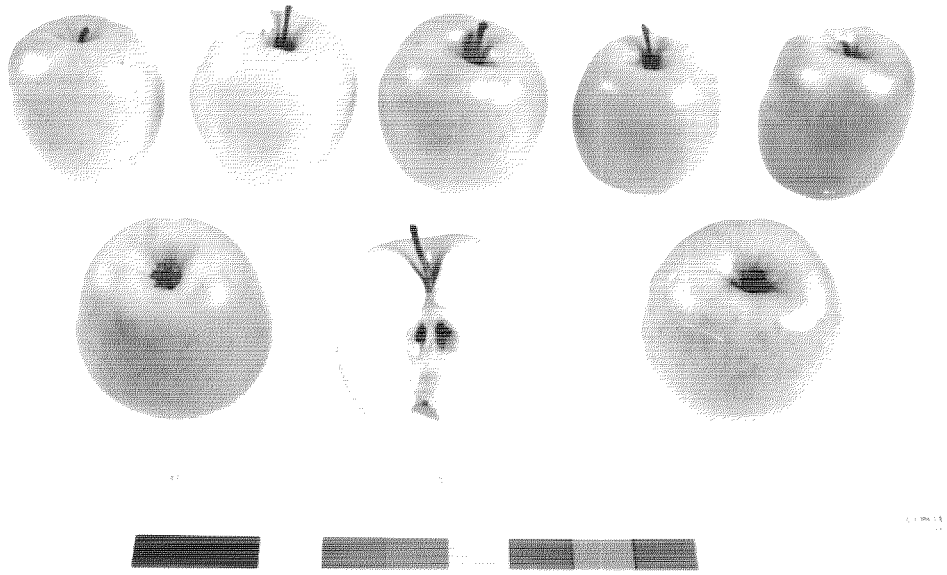
Figure 2:
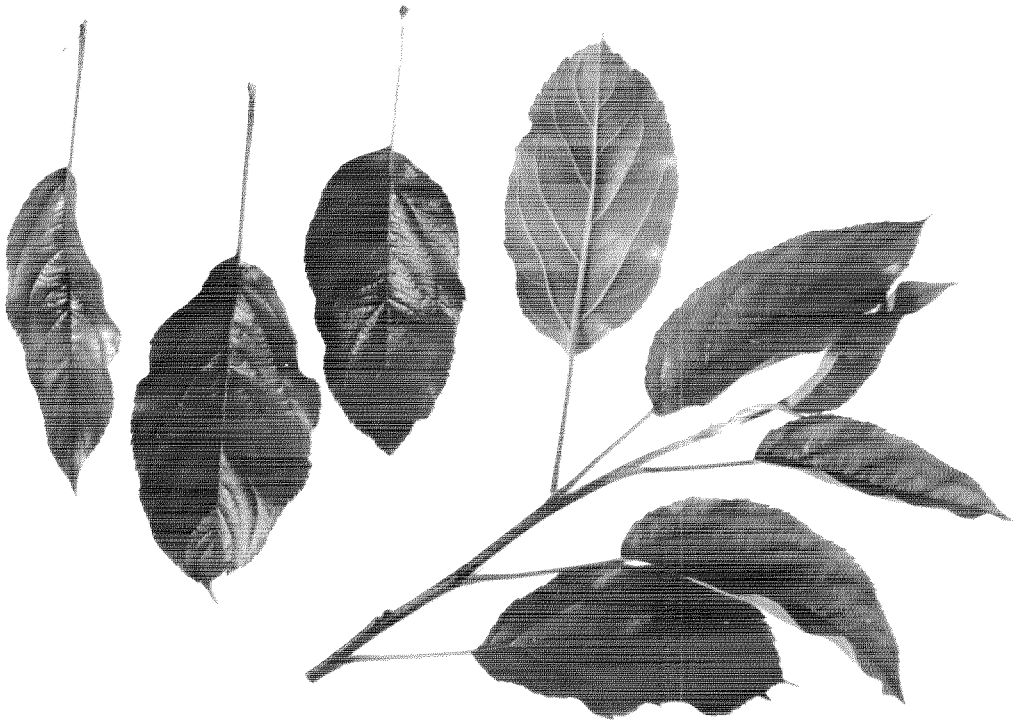
FIG. 2 illustrates the upper and under surfaces of typical leaves of the new cultivar in various stages of maturity wherein a younger leaf is depicted at the extreme left.
Figure 3:
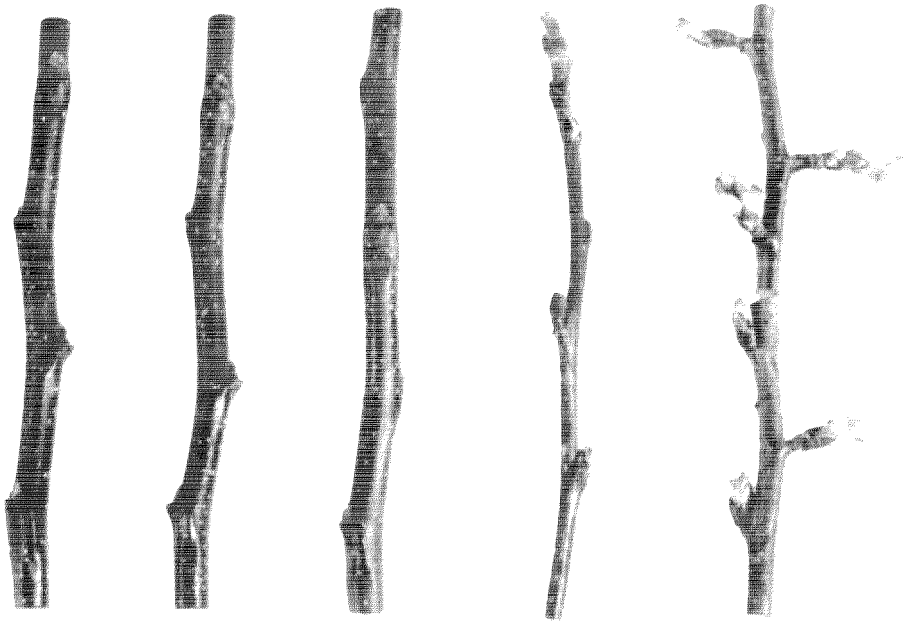
FIG. 3 illustrates typical budwood specimens of the new cultivar including dormant buds (left) and flower buds in the initial stage of opening (right).

The following is a detailed description of the new cultivar of the present invention. The description is based upon the observation of plants when grown at Malicorne, Commentry, France while budded on PAJAM® brand of 2 Cepiland rootstock. The chart used in the identification of colors is that of The Royal Horticultural Society, London, England (R.H.S. Colour Chart). Coloration in common terms also is provided wherein such coloration is to be accorded its ordinary dictionary significance.

Classification: *Malus domestica* Borkh.

Tree: Semi-upright, and dense with medium to strong vigor. A typical 5 year old tree when grown on M9 rootstock, while supported, commonly assumes a height of approximately 3.5 meters and a width of approximately 1.5 meters. Such dimensions are influenced by the exact nature of the training system that is utilized.

*Current season's shoots.*—Very slight pubescence, leaves extend upwards, leaves are elongated, the position of maximum leaf breadth approximates the center, the leaves commonly are saucered, biserrate leaf margins are exhibited, the apex of the leaves is acuminate, the leaves possess a rounded base, the mature leaves are medium green in coloration, Green Group 137B on the obverse, and possess medium glossy upper surfaces, the petioles are long and sometimes bear a tinge of red, Red Group 53C, the stipules are long in length and are much longer than broad, and a small substipule at the base of the stipule commonly is present. The mature leaves commonly are approximately 9 cm. in length and approximately 5.5 cm. in width.

*Wood and bark.*—One year-old wood commonly is reddish brown and downy in appearance and commonly possesses approximately 8 lenticels per $cm.^2$. Two year-old wood commonly is silvery brown with a rough aspect and commonly possesses in excess of 12 lenticels per $cm.^2$. The bark coloration commonly is Greyed-Green Group 197A.

*Dormant one year-old shoots.*—Absent or very weak pubescence on upper one-half, medium in thickness, relatively long internode lengths, medium number of medium-sized lenticels commonly are present, the pubescence of the wood buds is very slight, and the shoots tend to be more less straight and are not distinctly curved or zig-zagged.

Flowers: Intermediate flowering season similar to that of 'Cox's Orange Pippin'. The typical bloom date at Malicorne also is similar to that of the 'Golden Delicious Cultivar' and is approximately April 25th.

*Bud color.*—Spinel Red, Red Group 54B.

*Bud frequency.*—Medium number of buds per truss and similar to the 'Goldensheen' variety.

*Bud size.*—Commonly approximately 0.8 cm. in length and approximately 0.5 cm. in width.

*Petal bearing.*—Commonly possess a sharp base angle, and are substantially disjointed in the relation of petal margins.

*Petal configuration.*—Commonly are relatively long and a possess a greater length than width with moderate petal pubescence.

*Flower shape.*—Moderately cupped.

Figure 4:
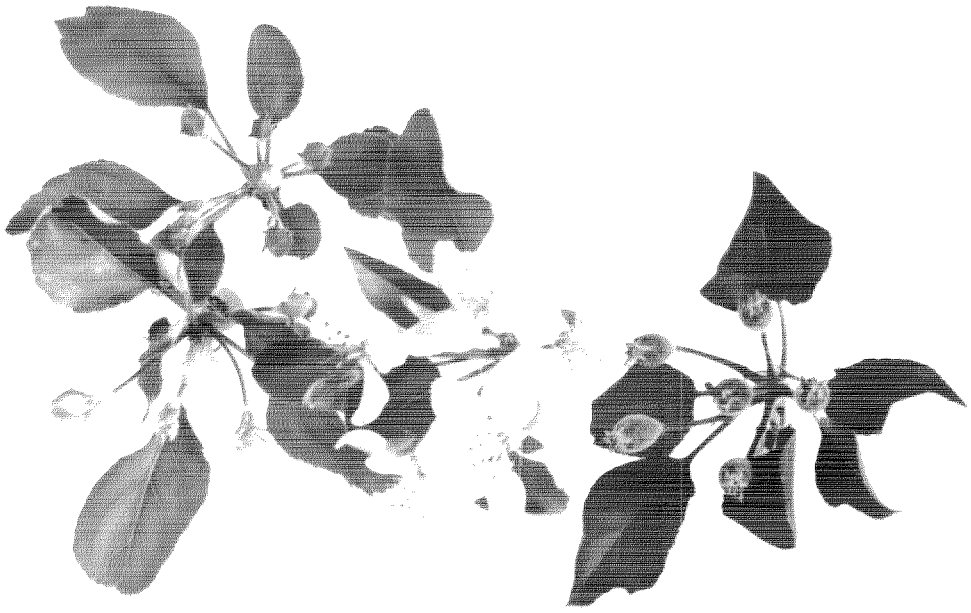
FIG. 4 illustrates at the left typical flower buds in more advanced stages of opening and the right initial fruit set.
Figure 5:
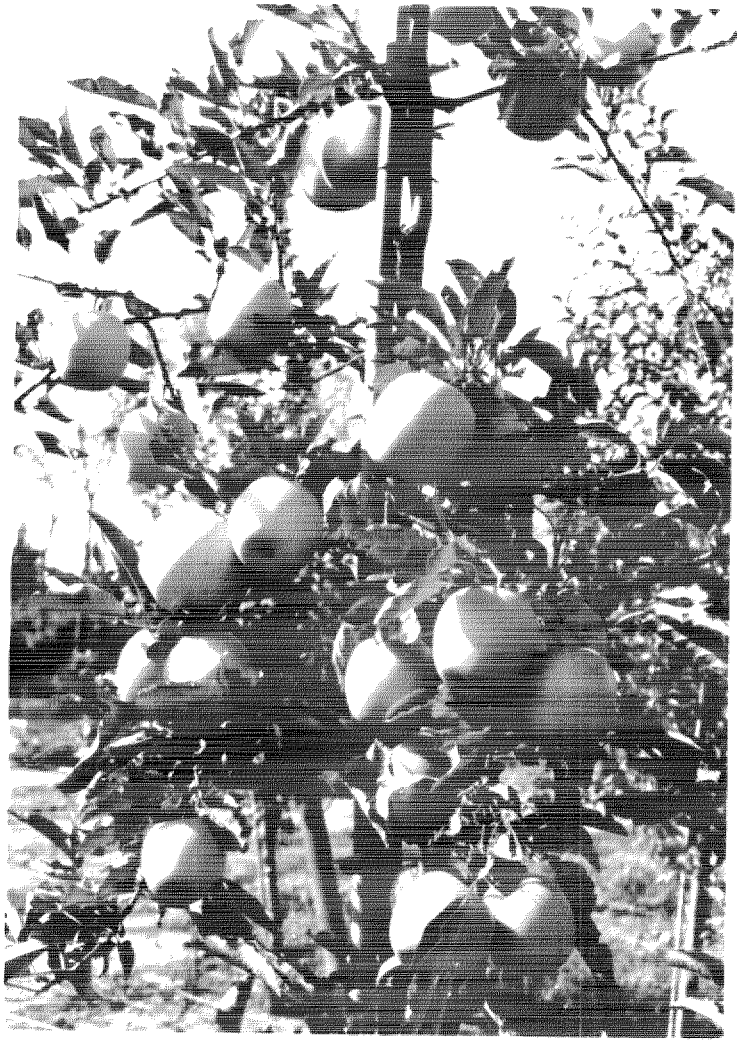
FIG. 5 illustrates the growth habit of a typical tree of the new cultivar while partially supported by a pole wherein an abundant fruit crop is visible prior to full maturity.

*Flower size.*—Large, but commonly the petal size and the flower size are smaller than those of the 'Golden Delicious' variety. See FIG. 4 were dimensions in centimeters are indicated.

*Sepals.*—Long, tapered, longer than broad, primarily green in coloration near Green Group 137D to 138A, recurved, and commonly are disposed in an erect manner.

*Pedicels.*—Long, and commonly range from approximately 3.5 to 3.8 cm. in length.

*Stamens.*—Semi-spreading and medium in number.

*Styles.*—Arranged at substantially the same height as the stamens, fused at the base as can be observed following removal of stamens, moderate in pubescence at the point of fusion, and commonly possess very slight pubescence at the base.

*Dormant fruit buds.*—Ovoid, moderately pointed at the apex, possess very slight pubescence, and are relatively large in size.

Fruit:

*Bearing habit.*—On tips of shoots.

*Size.*—Medium to large, commonly approximately 7 cm. in the axial direction and approximately 6.8 cm. transverse to the axial direction.

*Form.*—Oblong-conical configuration, commonly very slightly longer than broad, slightly asymmetric, approximately 5 ribs at crown at eye, and commonly no significant difference in configuration between the terminal fruits and the other fruits.

*Cavity.*—Deep, medium breadth, with acute angle of stock cavity, slight to moderate russet of the cavity that commonly is netted in appearance, and commonly with bright green areas, Yellow-Green Group 145A, in the stalk cavity. Commonly the cavity depth is approximately 1.9 cm. and the cavity breadth is approximately 1.5 cm.

*Basin.*—Medium in depth and breadth, the angle of the basin is acute, medium ribbing is present in the basin, and pubescence tends to be absent. Commonly the basin depth is approximately 2.2 cm. and the basin breadth is approximately 1.3 cm.

*Stem.*—Slender, long to very long, and extends much beyond the cavity. Commonly the stems are approximately 3.5 cm. in length and approximately 0.2 cm. in width.

*Picking time.*—Mid-season to late season and similar to the 'Golden Delicious' variety. Typical first and last picking dates at Malicorne are approximately September 25th and October 5th.

*Skin.*—Smooth, moderately shiny, not greasy, bloom is absent, free of a tendency to crack, tough, and possesses only a slight tendency to bruise.

*Lenticels.*—Numerous and large, angular and stellate in configuration, and free of raised russet lenticels.

*Ground color.*—Deep yellow, Yellow-Orange Group 16A, when mature (as illustrated).

*Over color.*—Orange of pale to medium intensity, Yellow-Orange Group 22A when present on mature fruit (as illustrated) and commonly extends over approximately 25 to 50 percent, or more, of the skin. The extent of the overcolor is influenced by the position of the fruit on the tree and the level of sunlight that is encountered during ripening. Very slight ribs sometimes are apparent, and very slight to moderate fine golden silvery russet, Grey-Brown Group 199B, that sometimes is netted in appearance commonly is present around the cavity and on the cheeks.

*Flesh.*—Medium to juicy and possesses a very slight tendency to brown upon the passage of time (i.e., after one hour). Texture. Firm. Color. Yellow, Yellow Group 13D, (as illustrated in FIG. 1 at the bottom row center). Flavor. Strong in sweetness and acidity, aromatic and aniseed.

*Core.*—Medium in size, and commonly approximately 2.5 cm. in length.

*Distinctness of core.*—Strong in longitudinal cross-section.

*Location of core.*—Median with respect to the longitudinal section.

*Shape of core.*—Oval in longitudinal section.

*Length of cells.*—Long in longitudinal section, and commonly approximately 1.1 cm. in length.

*Breadth of cells.*—Medium in longitudinal section, and commonly approximately 0.5 cm. in breadth.

*Configuration of cells.*—Obovate.

*Apex of cells.*—Mucronate in longitudinal section.

*Aperture of cells.*—Absent to narrow openness in cross-section.

*Number of fully developed seeds.*—Medium, and approximately five.

*Seed size.*—Approximately 1 cm. in length and approximately 0.5 cm. in width.

*Seed configuration.*—Obovate, longer than broad, and possess an acuminate apex.

*Seed coloration.*—Pale buff brown to brown, Greyed-Orange Group 166A.

*Keeping quality.*—Approximately six months in regular cold storage, and approximately ten months in controlled atmosphere storage.

*Shipping quality.*—Excellent.

Resistance to diseases: Not resistant to apple scab (Venturia), mildew, and canker (Nectria).

I claim:

1. A new and distinct cultivar of apple tree having the following combination of characteristics:

(a) forms attractive yellow fruit of excellent flavor and texture when mature commonly possessing an orange overcolor on a portion of the skin, (b) forms fruit flesh that well resists darkening upon exposure to ambient conditions, (c) forms attractive medium green foliage having an acuminate apex and a rounded base, and (d) commonly yields an apple crop mid to late in the season;

substantially as herein shown and described.

* * * * *